(12) United States Patent
Psaras et al.

(10) Patent No.: US 12,221,506 B2
(45) Date of Patent: Feb. 11, 2025

(54) ZIRCONIUM POLYMER COMPOSITION WITH METAL PARTICLES HAVING BIOLOGICAL CONTAMINANT REMOVAL PROPERTIES

(71) Applicant: Neo Chemicals & Oxides, LLC, Greenwood Village, CO (US)

(72) Inventors: Dimitrios Psaras, Bound Brook, NJ (US); Mason Reames Haneline, Orange, CA (US); Steven P. Williams, Oxfordshire (GB)

(73) Assignee: NEO Chemicals & Oxides, LLC, Greenwood Village, CO (US)

( * ) Notice: Subject to any disclaimer, the term of this patent is extended or adjusted under 35 U.S.C. 154(b) by 136 days.

(21) Appl. No.: 17/712,947

(22) Filed: Apr. 4, 2022

(65) Prior Publication Data
US 2022/0325014 A1   Oct. 13, 2022

Related U.S. Application Data

(60) Provisional application No. 63/170,279, filed on Apr. 2, 2021.

(51) Int. Cl.
| | |
|---|---|
| *C08F 30/04* | (2006.01) |
| *A61L 9/00* | (2006.01) |
| *C02F 1/50* | (2023.01) |
| *C08K 3/28* | (2006.01) |

(52) U.S. Cl.
CPC ............... *C08F 30/04* (2013.01); *A61L 9/00* (2013.01); *C02F 1/50* (2013.01); *C08K 3/28* (2013.01); *C02F 2303/04* (2013.01)

(58) Field of Classification Search
None
See application file for complete search history.

(56) References Cited

U.S. PATENT DOCUMENTS

| 3,518,050 A | 2/1972 | Woodhead |
|---|---|---|
| 8,142,938 B2 | 3/2012 | Khasin et al. |
| (Continued) | | |

FOREIGN PATENT DOCUMENTS

| CN | 101081365 A | 12/2007 |
|---|---|---|
| CN | 101305735 A | 11/2008 |
| (Continued) | | |

OTHER PUBLICATIONS

WO-2018021106-A1, 2018, machine translation (Year: 2018).*

(Continued)

*Primary Examiner* — Satya B Sastri
(74) *Attorney, Agent, or Firm* — Melissa M. Hayworth; George C. Lewis; Merchant & Gould, P.C.

(57) ABSTRACT

A zirconium polymer composition comprising a zirconium polymer selected from the group consisting of polymeric zirconium oxychloride, polymeric zirconium acetate, and polymeric zirconium nitrate and having metal particles thereon is beneficial to aid in the removal of biological contaminants, such as bacteria, virus, yeast, algae, and amoeba, from fluids, including air and water. In this composition, the metal is selected from the group consisting of aluminum (Al), antimony (Sb), arsenic (As), barium (Ba), silicon (Si), boron (B), copper (Cu), gold (Au), lead (Pb), mercury (Hg), nickel (Ni), silver (Ag), thorium (Th), tin (Sn), zinc (Zn), and mixtures thereof, and the metal particles are about 0.001% by weight to about 30% by weight of the composition. These zirconium polymer compositions are used in methods for removing biological contaminants from fluids.

29 Claims, 5 Drawing Sheets

(56) References Cited

U.S. PATENT DOCUMENTS

| | | |
|---|---|---|
| 8,475,921 B2 | 7/2013 | Kayama et al. |
| 8,900,750 B2 | 12/2014 | Khasin et al. |
| 9,666,874 B2 | 5/2017 | Khasin et al. |
| 9,686,997 B2 | 6/2017 | Pagotto Sim Es et al. |
| 9,941,516 B2 | 4/2018 | Khasin et al. |
| 2003/0069132 A1 | 4/2003 | Woodhead |
| 2011/0027385 A1* | 2/2011 | Cairns ................ C25D 5/34 |
| | | 977/773 |
| 2020/0404925 A1 | 12/2020 | Hayashi et al. |
| 2023/0392263 A1 | 12/2023 | Gock et al. |

FOREIGN PATENT DOCUMENTS

| | | |
|---|---|---|
| EP | 1918046 B1 | 4/2012 |
| EP | 2684602 B1 | 6/2016 |
| EP | 2049449 B1 | 7/2018 |
| JP | 07033616 A | 2/1995 |
| JP | 11228320 A | 8/1999 |
| JP | 2988811 B2 | 12/1999 |
| JP | 2004161632 A * | 6/2004 |
| JP | 2013216596 A | 10/2013 |
| WO | 2007011062 A1 | 1/2007 |
| WO | 2008017719 A3 | 4/2008 |
| WO | 2013033802 A1 | 3/2013 |
| WO | WO-2018021106 A1 * | 2/2018 ............. A01N 25/34 |
| WO | 2019188353 A1 | 10/2019 |
| WO | 2020257919 A1 | 12/2020 |
| WO | 2021084140 A2 | 5/2021 |

OTHER PUBLICATIONS

JP-2004161632-A, 2004, machine translation (Year: 2004).*
Search Report and Written Opinion from International Application No. PCT/US2022/023336 mailed Jul. 11, 2022.

* cited by examiner

ZIRCONIUM POLYMER COMPOSITION WITH METAL PARTICLES HAVING BIOLOGICAL CONTAMINANT REMOVAL PROPERTIES

RELATED APPLICATION

This application claims priority to and benefit of U.S. Provisional Application No. 63/170,279 filed Apr. 2, 2021, the contents of which are hereby incorporated by reference herein their entirety.

FIELD OF THE INVENTION

This disclosure relates to a zirconium polymer composition having antiviral, antibacterial, and/or antifungal properties. The zirconium polymer composition comprises a polymeric zirconium and has metal particles thereon. This composition has biological contaminant removal properties, and as such, has uses for removing bacterial or virus from fluids, including air and water, and/or surfaces.

Introduction

Various technologies have been used to remove biological contaminants from air and aqueous systems. Examples of such techniques include adsorption on high surface area materials, such as alumina, filters with pore sizes smaller than the biological contaminants, and the use of highly oxidative materials such as chlorine and bromine. Certain metals have also found use because they exhibit the oligodynamic effect which is the biocidal effect of metals. Metals known to exhibit the oligodynamic effect are Al, Sb, As, Ba, Si, B, Cu, Au, Pb, Hg, Ni, Ag, Th, Sn, and Zn. Silver has been commonly used and using finely divided particles leads to more surface area which leads to more efficient biocidal results. Incorporation of these into technologies for air or aqueous system treatment remains a challenge as the toxicity towards human and animal life and the cost are major concerns.

The need for effective and inexpensive antimicrobial materials to remove bacteria and/or viruses from fluids, including air, water, and other aqueous systems, remains.

SUMMARY

This disclosure relates generally to a zirconium polymer composition having metal particles supported thereon for removing bacteria, viruses and other microbial contaminants from air and aqueous liquid streams and is particularly concerned with removing bacteria and viruses from air and water, whether the microbes are in high or very low concentrations, using polymeric zirconium having metal particles dispersed thereon. These polymeric zirconium compositions have unique structural and electrochemical properties as disclosed herein.

As disclosed herein is a zirconium polymer composition. The zirconium polymer composition comprises a zirconium polymer selected from the group consisting of polymeric zirconium oxychloride, polymeric zirconium acetate, and polymeric zirconium nitrate and has metal particles thereon, wherein the metal is selected from the group consisting of aluminum (Al), antimony (Sb), arsenic (As), barium (Ba), silicon (Si), boron (B), copper (Cu), gold (Au), lead (Pb), mercury (Hg), nickel (Ni), silver (Ag), thorium (Th), tin (Sn), zinc (Zn), and mixtures thereof. The metal particles are about 0.001% by weight to about 30% by weight of the zirconium polymer composition.

As further disclosed is a method for making a zirconium polymer composition. The method comprises (i) dissolving an organic binder in water to form a mixture; (ii) to the mixture of (i) adding: (a) soluble metal salt wherein the metal is selected from the group consisting of aluminum (Al), antimony (Sb), arsenic (As), barium (Ba), silicon (Si), boron (B), copper (Cu), gold (Au), lead (Pb), mercury (Hg), nickel (Ni), silver (Ag), thorium (Th), tin (Sn), zinc (Zn), and mixtures thereof, (b) a reducing agent, (c) zirconyl nitrate solution, zirconyl chloride solution, or zirconyl acetate solution, and (d) a chelating agent to create a solution; (iii) removing liquid of the solution of (ii) to obtain the zirconium polymer composition comprising a zirconium polymer selected from the group consisting of polymeric zirconium oxychloride, polymeric zirconium acetate, and polymeric zirconium nitrate and having metal particles thereon as a precipitate; and (iv) collecting and drying the zirconium polymer composition. In some embodiments, the method includes an optional step of rinsing with water prior to drying to remove residual reactants not incorporated into the polymeric zirconium framework.

In certain embodiments, the organic binder is selected from the group consisting of polyurethane, polyvinylpyrolidone, polyvinyl alcohol, linseed oil, and mixtures thereof. In certain embodiments, the reducing agent is selected from the group consisting of sucrose, ascorbic acid, and mixtures thereof. In certain embodiments, the chelating agent is selected from the group consisting of citric acid, malonic acid, succinic acid, glutaric acid, adipic acid, and mixtures thereof.

Additionally disclosed are methods of using the zirconium polymer composition for removing bacteria, viruses and other microbial contaminants from air and liquid streams. Typically, the contacting of the zirconium polymer compositions containing polymeric zirconium oxychloride, polymeric zirconium acetate, or polymeric zirconium nitrate and having metal particles thereon with the gaseous or aqueous stream can reduce the biological contaminant level in the gaseous or aqueous stream by more than about 75%. More typically, the contacting of the polymeric zirconium composition with the gaseous or aqueous stream can reduce the biological contaminant level in the gaseous or aqueous stream by more than about 80%, more typically more than about 85%, more typically more than about 90%, more typically more than about 95%, more typically more than about 97.5%, more typically more than about 99%, and even more typically more than about 99.5%. These methods function by contacting the gaseous or aqueous stream with the zirconium polymer compositions containing polymeric zirconium oxychloride, polymeric zirconium acetate, or polymeric zirconium nitrate and having metal particles thereon.

As described herein are methods for removing biological contaminants from a gaseous stream. The method comprises providing the zirconium polymer composition as described herein; contacting the zirconium polymer composition with a biological contaminant-containing gaseous stream, wherein the biological contaminant is selected from the group consisting of a bacterium, a yeast, an algae, a virus, and mixtures thereof and removing at least about 99% of the biological contaminant. Also as described herein are methods for removing biological contaminants from an aqueous stream. The method comprises providing the zirconium polymer composition as described herein; contacting the zirconium polymer composition with a biological contaminant-containing gaseous stream, wherein the biological contaminant is selected from the group consisting of a bacterium, a yeast, an algae, a virus, and mixtures thereof; and removing at least about 99% of the biological contaminant.

Figure 1:
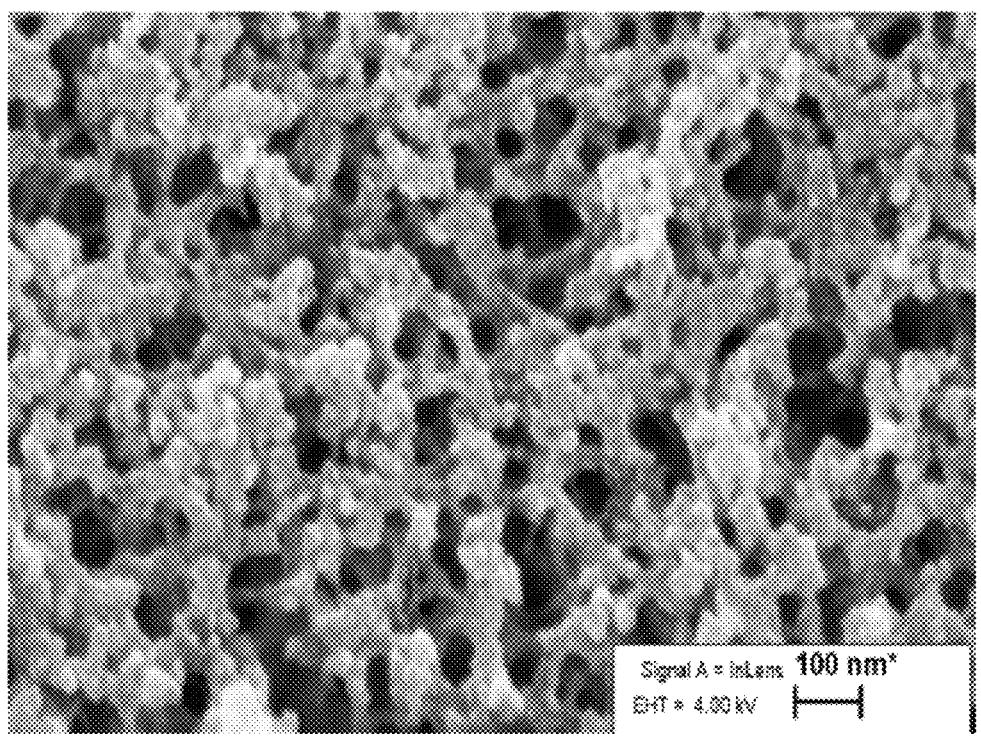
FIG. 1 is a SEM image of the composition of Example 1 with a scale bar of 100 nm.

FIG. 3 is a TEM image of the composition of Example 1 with a scale bar of 20 nm. The box indicates the zoom area presented in FIG. 4.

FIG. 4 is a TEM image of the boxed area from FIG. 3. The scale bar is 10 nm. The right side of the image shows the Ag mapping where metallic Ag is indicated by the lighter spots.

FIG. 5 is the XRD pattern of the composition of Example 1 which shows only peaks for metallic Ag.

FIG. 6 is the Temperature Programmed Desorption of $CO_2$ Profile for the composition of Example 1.

FIG. 7 is the Hydrogen Temperature Programmed Reduction Profile for the composition of Example 1.

DETAILED DESCRIPTION

Before the zirconium polymer composition and methods are disclosed and described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting. It must be noted that, as used in this specification, the singular forms "a," "an," and "the" include plural referents unless the context clearly dictates otherwise. Thus, for example, reference to "a silver particle" is not to be taken as quantitatively or source limiting, reference to "a step" may include multiple steps, reference to "producing" or "products" of a reaction or treatment should not be taken to be all of the products of a reaction/treatment, and reference to "treating" may include reference to one or more of such treatment steps. As such, the step of treating can include multiple or repeated treatment of similar materials/streams to produce identified treatment products.

Numerical values with "about" include typical experimental variances. As used herein, the term "about" means within a statistically meaningful range of a value, such as a stated particle size, concentration range, time frame, molecular weight, temperature, or pH. Such a range can be within an order of magnitude, typically within 10%, and even more typically within 5% of the indicated value or range. Sometimes, such a range can be within the experimental error typical of standard methods used for the measurement and/or determination of a given value or range. The allowable variation encompassed by the term "about" will depend upon the particular system under study, and can be readily appreciated by one of ordinary skill in the art. Whenever a range is recited within this application, every whole number integer within the range is also contemplated as an embodiment of the invention.

This disclosure relates generally to a zirconium polymer composition comprising a polymeric zirconium and having metal particles supported thereon. This zirconium polymer composition is capable of removing biological contaminants from fluids, including liquids and air. Specifically, the zirconium polymer composition is capable of removing bacteria, viruses, and other microbial contaminants from air and aqueous liquid streams. These bacteria include gram positive and gram negative bacteria and include for example, *Streptococcus, Staphylococcus, E. coli, Escherichia coli*, Methicillin-resistant *Staphylococcus aureus* (MRSA), and the like. These viruses include for example coronaviruses, vaccinia, poliovirus, morbillivirus, and the like. Other microbial contaminants include for example *Trichophyton mentagrophytes*.

The zirconium polymer composition comprises a polymeric zirconium selected from the group consisting of polymeric zirconium oxychloride, polymeric zirconium acetate, and polymeric zirconium nitrate and has metal particles thereon.

The polymeric zirconium of the composition has a lower anion to Zr ratio than the predicted stochiometric molar ratio. For example, it is expected that the molar ratio of $NO_3$ to Zr should be 2:1. But in polymeric zirconium nitrate of the present composition, the polymers have a $NO_3$ to Zr molar ratio of about 0.5:1 to about 1.5:1. These polymers are prepared from an aqueous solution and contain lattice water and both covalent and ionic nitrate. These are large cationic polymers in which the units are joined by nitrato and diol bridges. As such, the polymeric zirconium can contain polymeric molecules with repeating units of Zr, O, and H atoms. These type of polymeric zirconium nitrate are known to those of skill in the art and are described, for example, in U.S. Pat. No. 3,518,050.

Unique to this disclosure, these novel zirconium polymer compositions have metal particles thereon. The metal particles are distributed or dispersed throughout the zirconium polymer composition. In preferred embodiments, the metal particles are on the surface of the zirconium polymer composition. It also can be described as the metal particles being supported on the zirconium polymer composition. In certain embodiments, the metal particles are distributed or dispersed on the surface of the zirconium polymer composition in a random distribution.

The metal of the metal particles on the zirconium polymer composition is a metal selected from the group consisting of aluminum (Al), antimony (Sb), arsenic (As), barium (Ba), silicon (Si), boron (B), copper (Cu), gold (Au), or lead (Pb), mercury (Hg), nickel (Ni), silver (Ag), thorium (Th), tin (Sn), zinc (Zn), and mixtures thereof.

In certain embodiments, the metal is silver. In certain of these embodiments, the metal is silver and the silver is metallic.

In certain embodiments the polymeric zirconium is polymeric zirconium nitrate and the metal particles are silver.

The composition comprising polymeric zirconium and having metal particles thereon has a metal content of about 0.001% by weight to about 30% by weight. As such, the composition as disclosed herein is a zirconium polymer selected from polymeric zirconium oxychloride, polymeric zirconium acetate, or polymeric zirconium nitrate and has metal particles thereon, wherein the metal is selected from the group consisting of aluminum (Al), antimony (Sb), arsenic (As), barium (Ba), silicon (Si), boron (B), copper (Cu), gold (Au), or lead (Pb), mercury (Hg), nickel (Ni), silver (Ag), thorium (Th), tin (Sn), zinc (Zn), and mixtures thereof, wherein the metal particles are about 0.001% by weight to about 30% by weight of the composition. In certain embodiments, the metal particles are about 0.05% to about 15% by weight of the composition. In other embodiments, the metal particles are about 0.05% to about 10% by weight of the composition. In further embodiments, the metal particles are about 0.05% to about 5% by weight of the composition.

In certain embodiments, the metal supported on the zirconium polymer composition is silver, and the silver content of the overall composition is 0.001% by weight to about 30% by weight of the composition. In certain embodiments, the silver is about 0.05% to about 15% by weight of the composition. In other embodiments, the silver is about 0.05% to about 10% by weight of the composition. In further embodiments, the silver is about 0.05% to about 5% by weight of the composition.

In certain of these specific silver particle embodiments, the polymeric zirconium is polymeric zirconium nitrate.

The zirconium polymer composition may further comprise one or more of an organic binder, a reducing agent, and a chelating agent. In certain embodiments, the organic binder is selected from the group consisting of polyvinyl alcohol (PVA), polyurethane (PU), polyvinylpyrollidone (PVP), linseed oil, and mixtures thereof. In certain embodiments, the reducing agent is selected from the group consisting of sucrose, ascorbic acid, and mixtures thereof. The reducing agent reduces the metal particles to metallic. In certain embodiments, the chelating agent is selected from the group consisting of citric acid, malonic acid, succinic acid, glutaric acid, adipic acid, and mixtures thereof. In embodiments where present, these optional additional components (i.e, organic binder, reducing agent, and/or chelating agent) become part of the polymeric zirconium framework of the zirconium polymer composition. These additional components may be present individually or in any combination thereof including all three.

For the purposes of this application unless otherwise specified, weight (wt) % of the composition with regard to the metal particles is the % weight relative to the total weight of the composition, without regard to the amount of water present and without regard to trace elements or salts unrelated to the metal particles or the polymeric zirconium framework.

These zirconium polymer compositions containing polymeric zirconium oxychloride, polymeric zirconium acetate, or polymeric zirconium nitrate and having metal particles thereon remove biological contaminants from fluids, including air and water, or surfaces.

Although the processes of using these compositions are primarily envisioned for removing bacterial and viral contaminants from air or drinking water and groundwater, it will be understood that the compositions and processes can be used to treat any gaseous or aqueous liquid feed that contains undesirable amounts of microbial contaminants. Examples of such gaseous feeds include, among others, building ventilation systems, aircraft or vehicle ventilation systems, and ambient room air. Examples of such liquid feeds include, among others, tap water, well water, surface waters, such as water from lakes, ponds and wetlands, agricultural waters, wastewater from industrial processes, and geothermal fluids. These compositions can also be incorporated into plastics for touch surfaces or containers that remove undesirable amounts of microbial contaminants by contact.

The compositions as disclosed herein can remove bacteria, viruses, and other microbial contaminants (hereinafter the "target contaminant") from a gaseous or liquid feed. Other target contaminants include active and inactive biological materials (such as living and non-living biological matter (e.g., bacteria, viruses, fungi, toxins, biological residue and other microbes)), pharmaceuticals, and mixtures and combinations thereof.

The processes of using the compositions as disclosed herein are primarily envisioned for removing biological contaminants from a gaseous or an aqueous stream through contacting these streams with the zirconium polymer compositions containing polymeric zirconium oxychloride, polymeric zirconium acetate, or polymeric zirconium nitrate and having metal particles thereon. The gaseous stream can be one or more of an ambient air source or more supply air for a ventilation system that contains undesirable amounts of biological and/or other contaminants. The aqueous stream can be one or more of a drinking water and groundwater source that contains undesirable amounts of biological and/or other contaminants. Furthermore, the aqueous stream can include without limitation well waters, surface waters (such as water from lakes, ponds and wetlands), agricultural waters, wastewater from industrial processes, and geothermal waters.

Generally, the zirconium polymer compositions containing polymeric zirconium oxychloride, polymeric zirconium acetate, or polymeric zirconium nitrate and having metal particles thereon can be used to treat any gaseous or aqueous stream containing a biological contaminant. The zirconium polymer compositions containing polymeric zirconium oxychloride, polymeric zirconium acetate, or polymeric zirconium nitrate and having metal particles thereon have a number of properties that are particularly advantageous for biological contaminant removal. These properties include surface area, pore volume, pore size, and/or particle size as described below.

Contacting of the zirconium polymer compositions containing polymeric zirconium oxychloride, polymeric zirconium acetate, or polymeric zirconium nitrate and having metal particles thereon with the gaseous or aqueous stream containing the biological contaminant effectively can reduce biological contaminant level in the gaseous or aqueous stream. Typically, the contacting of the zirconium polymer compositions containing polymeric zirconium oxychloride, polymeric zirconium acetate, or polymeric zirconium nitrate and having metal particles thereon with the gaseous or aqueous stream can reduce the biological contaminant level in the gaseous or aqueous stream by more than about 75%. More typically, the contacting of the polymeric zirconium composition with the gaseous or aqueous stream can reduce the biological contaminant level in the gaseous or aqueous stream by more than about 80%, more typically more than about 85%, more typically more than about 90%, more typically more than about 95%, more typically more than about 97.5%, more typically more than about 99%, and even more typically more than about 99.5%.

The zirconium polymer compositions containing polymeric zirconium oxychloride, polymeric zirconium acetate, or polymeric zirconium nitrate and having metal particles thereon have a surface area that assists in providing the biological contaminant removal properties.

As described herein, the surface area is the apparent surface area of the compositions as determined by using a Micromeritics ASAP 2000 system and nitrogen at about 77 Kelvin. The procedure outlined in ASTM International test method D 3663-03 (Reapproved 2008) was used but with one significant exception. It is well known that a "BET Surface Area" determination is not possible for materials that contain microporosity. Recognizing that the surface area is an approximation, the values reported are labeled "apparent surface area" values rather than "BET surface area" values. In compliance with commonly accepted procedures, the determination of apparent surface area, the application of the BET equation was limited to the pressure range where the term na(1-P/Po) of the equation continuously increases with P/Po. The out gassing of the sample was done under nitrogen at about 300 degrees Celsius for about 2 hours.

The zirconium polymer compositions containing polymeric zirconium oxychloride, polymeric zirconium acetate, or polymeric zirconium nitrate and having metal particles thereon commonly can have a surface area from about 10 to about 150 m$^2$/g, more commonly from about 10 to about 100 m$^2$/g, more commonly from about 15 to about 80 m$^2$/g, or even more typically from about 20 to about 40 m$^2$/g. While not wanting to be bound by any theory, it is believed that the surface area can affect and improve the removal of the biological contaminant from a gaseous or an aqueous stream.

It can be appreciated that the polymeric zirconium compositions having the above described surface areas also can have any one or more of the below average pore volumes, average pore sizes, and particle sizes.

The zirconium polymer compositions containing polymeric zirconium oxychloride, polymeric zirconium acetate, or polymeric zirconium nitrate and having metal particles thereon typically have an average (mean, median, and mode) pore volume (as determined by N$_2$ adsorption) of about 0.01 cm$^3$/g to about 0.5 cm$^3$/g, and more typically of about 0.05 cm$^3$/g to about 0.2 cm$^3$/g, and even more typically of about 0.07 cm$^3$/g to about 0.15 cm$^3$/g. While not wanting to be bound by any theory it is believed that the average pore volume can affect and improve the removal of the biological contaminant from an aqueous or gaseous stream.

It can be appreciated that the polymeric zirconium compositions can have any one of the described average pore volumes in combination with any one or more of the above surface areas and the below average pore sizes and particle sizes.

The zirconium polymer compositions containing polymeric zirconium oxychloride, polymeric zirconium acetate, or polymeric zirconium nitrate and having metal particles thereon generally have an average (mean, median, and mode) pore size (as determined by the Barrett-Joyner-Halenda (BJH) method) of more than about 1 nm to about 25 nm, more generally of more than about 1 nm to about 15 nm, and more generally of about 1 nm to about 10 nm. While not wanting to be bound by any theory, it is believed that the average pore size can affect and improve the removal of the biological contaminant from an aqueous or gaseous stream.

It can be appreciated that the polymeric zirconium compositions can have any one of the described average pore sizes in combination with any one or more of the above surface areas and average pore volumes and the below particle sizes. For example, the polymeric zirconium compositions can have a surface area of about 10 m$^2$/g to about 100 m$^2$/g, a pore volume of about 0.01 cm$^3$/g to about 0.5 cm$^3$/g and an average pore size of about 1 nm to about 25 nm.

The zirconium polymer compositions containing polymeric zirconium oxychloride, polymeric zirconium acetate, or polymeric zirconium nitrate and having metal particles thereon have one or both of the below described D50 and D100 particle sizes. While not wanting to be bound by any theory, it is believed that the particle size can affect and improve the removal of the biological contaminant from a gaseous or an aqueous stream.

Particle size analysis was done using a Microtrac S3500 particle size analyzer. A typical measurement is done by using approximately 0.2 grams of a powder sample, 20 ml of a 2% sodium hexametaphosphate solution is added to the sample. The sample+solution are then sonicated for approximately 3 minutes. A few drops of the sonicated solution are then added to the sample container of the instrument. The sample is again sonicated in the machine for another 3 minutes. Three consecutive runs are done by the machine according to the instrument manufacturer instruction manual. The three runs are averaged and the results recorded.

The zirconium polymer compositions containing polymeric zirconium oxychloride, polymeric zirconium acetate, or polymeric zirconium nitrate and having metal particles thereon generally have a particle size D50 of about 0.5 µm to 15 more typically of about 0.5 µm to about 5 and more typically of about 0.5 µm to about 2 µm.

The zirconium polymer compositions containing polymeric zirconium oxychloride, polymeric zirconium acetate, or polymeric zirconium nitrate and having metal particles thereon generally have a particle size D100 of about 2 µm to about 50 µm, more typically of about 2 µm to about 20 µm and more typically of about 2 µm to about 10 µm.

It can be appreciated that the polymeric zirconium compositions can have any one of the described D50 particle sizes in combination with any one or more of the D100 particles sizes, as well as the above described surface areas, average pore volumes and average pore sizes.

Generally, the zirconium polymer compositions containing polymeric zirconium oxychloride, polymeric zirconium acetate, or polymeric zirconium nitrate and having metal particles thereon have one or more hydrogen peak reduction temperatures. Generally, one peak occurs between about 100 and about 300° C. and a second peak occurs between about 400 and about 700° C. More generally, one peak occurs between about 120 and 200° C. and a second peak occurs between about 400 and 650° C. as measured by temperature programmed reduction. While not wanting to be bound by any theory, it is believed that the peak reduction temperature of the polymeric zirconium compositions can affect and improve the removal of the biological contaminant from a gaseous or an aqueous stream.

It can be appreciated that the polymeric zirconium compositions can have any one of the described peak reduction temperatures in combination with any one or more of the above described surface areas, average pore volumes, average pore sizes and particle sizes.

Generally, the zirconium polymer compositions containing polymeric zirconium oxychloride, polymeric zirconium acetate, or polymeric zirconium nitrate and having metal particles thereon have one or more peak temperatures in the temperature programmed desorption of carbon dioxide ($CO_2$) profile. Generally, one peak occurs between about 70 and 200° C. and a second peak occurs between about 350 and 650° C. More generally, one peak occurs between about 100 and 300° C. and a second peak occurs between about 350 and 500° C. as measured by temperature programmed reduction. While not wanting to be bound by any theory it is believed that the peak reduction temperature of the polymeric zirconium compositions can affect and improve the removal of the biological contaminant from a gaseous or an aqueous stream.

It can be appreciated that the polymeric zirconium compositions can have any one of the described peak temperatures in combination with any one or more of the above peak reduction temperatures, surface areas, average pore volumes, average pore sizes and particle sizes.

In some embodiments, the polymeric zirconium compositions having metal particles thereon can be deposited on or within a support material. As such, the polymeric zirconium compositions having metal particles can be deposited on one or more external and/or internal surfaces of the support material. It can be appreciated that persons of ordinary skill in the art generally refer to the internal surfaces of a support material as pores.

This support material also can be polyethylene and the polymeric zirconium compositions can be deposited on the surface or within the polyethylene. When used with polyethylene, the polymeric zirconium compositions having metal particles thereon can be incorporated into a plastic container or a plastic to be incorporated into a high touch surface, such as elevator buttons, escalator railing covers, stair railing covers, touch pads, and the like. When used with polyethylene, the polymeric zirconium compositions can be incorporated by mixing with polyethylene granules or powder. The polyethylene can be formed into an end use product as described above.

The polymeric zirconium compositions having metal particles thereon can be supported on the support material with or without a binder. In some embodiments, the polymeric zirconium compositions having metal particles can be applied to the support material using any conventional techniques, such as slurry deposition.

Contacting of the zirconium polymer compositions containing polymeric zirconium oxychloride, polymeric zirconium acetate, or polymeric zirconium nitrate and having metal particles thereon with the gaseous or liquid streams containing one or more biological contaminants have the property of effectively reducing one or more of biological contaminant levels in the gaseous or liquid stream. The zirconium compositions effectively reduce at least some, most, or all of the biological contaminants.

The term "some" refers to removing at least about 10% and no more than about 50% of the biological contaminant contained in the stream. The term "most" refers to removing more than about 50% to about 90% of the biological contaminant contained in the stream. The term "all" refers to removing more than about 90% to about 100% of the biological contaminant contained in the stream. More generally, the term "all" refers to removing more than 98%, 99%, or 99.5%, or to removing 99.9% of the biological contaminant contained in the stream.

Typically, the contacting of the zirconium polymer compositions containing polymeric zirconium oxychloride, polymeric zirconium acetate, or polymeric zirconium nitrate and having metal particles thereon with the gaseous or liquid stream can reduce the biological contaminant level in the gaseous or liquid stream by more than about 75%. More typically, the contacting of the polymeric zirconium composition with the gaseous or aqueous stream can reduce the biological contaminant level in the gaseous or liquid stream by more than about 80%, more typically more than about 85%, more typically more than about 90%, more typically more than about 95%, more typically more than about 97.5%, more typically more than about 99%, and even more typically more than about 99.5%.

Method of Making the Zirconium Polymer Composition

The present application relates to methods for making the zirconium polymer composition as disclosed herein. This method includes the steps of (i) dissolving an organic binder in water to form a mixture; (ii) to this mixture adding: (a) soluble metal salt wherein the metal is selected from the group consisting of aluminum (Al), antimony (Sb), arsenic (As), barium (Ba), silicon (Si), boron (B), copper (Cu), gold (Au), lead (Pb), mercury (Hg), nickel (Ni), silver (Ag), thorium (Th), tin (Sn), zinc (Zn), and mixtures thereof, (b) a reducing agent, (c) zirconyl nitrate solution, zirconyl chloride solution, or zirconyl acetate solution, and (d) a chelating agent to create a solution; (iii) removing liquid of the solution as created in (ii) to obtain the zirconium polymer composition as a precipitate; and (iv) collecting and drying the zirconium polymer composition. As such, the zirconium polymer composition is made by precipitating and reducing metal particles onto a polymeric zirconium.

In this embodiment of the method for making the zirconium polymer composition, the metal particles are formed during the formation of the composition by precipitation and reduction of a soluble salt of the metal. In some embodiments, the soluble salt is the nitrate salt of the metal. The metal is as described above, and is selected from the group consisting of aluminum (Al), antimony (Sb), arsenic (As), barium (Ba), silicon (Si), boron (B), copper (Cu), gold (Au), lead (Pb), mercury (Hg), nickel (Ni), silver (Ag), thorium (Th), tin (Sn), zinc (Zn), and mixtures thereof.

The zirconium polymer composition may further incorporate one or more of the organic binder, reducing agent, and chelating agent as used in the method of making the composition. The composition as collected optionally may be rinsed with water prior to drying to remove residual reactants not incorporated into the polymeric zirconium framework.

In certain embodiments, the organic binder is selected from the group consisting of polyvinyl alcohol (PVA), polyurethane (PU), polyvinylpyrollidone (PVP), linseed oil, and mixtures thereof The reducing agent in the reductive precipitation can be any reducing agent capable of reducing the metal ion to the zero-valent metal. In embodiments, the reducing agent is selected from the group consisting of sucrose, ascorbic acid, hydrogen gas, hydrazine, and mixtures thereof. In certain embodiments, the reducing agent is selected from the group consisting of sucrose, ascorbic acid, and mixtures thereof. The reducing agent reduces the soluble metal ions to metallic.

In certain embodiments, the chelating agent is selected from the group consisting of citric acid, malonic acid, succinic acid, glutaric acid, adipic acid, and mixtures thereof.

As such, the methods make the zirconium polymer composition as disclosed herein that comprises a zirconium polymer selected from the group consisting of polymeric zirconium oxychloride, polymeric zirconium acetate, and polymeric zirconium nitrate and has metal particles thereon, wherein the metal is selected from the group consisting of aluminum (Al), antimony (Sb), arsenic (As), barium (Ba), silicon (Si), boron (B), copper (Cu), gold (Au), lead (Pb), mercury (Hg), nickel (Ni), silver (Ag), thorium (Th), tin (Sn), zinc (Zn), and mixtures thereof. In this zirconium polymer composition, the metal particles are about 0.001% by weight to about 30% by weight of the composition. In certain embodiments, the metal particles are about 0.05% to about 15% by weight of the composition. In other embodiments, the metal particles are about 0.05% to about 10% by weight of the composition. In further embodiments, the metal particles are about 0.05% to about 5% by weight of the composition.

These zirconium polymer compositions are capable of reducing the concentration of microbes, including viruses and bacteria, from gaseous or aqueous streams.

In the methods for making the zirconium polymer compositions, the organic binder is dissolved in water, a soluble metal salt is added to the solution along with the polymeric zirconium, and one or more reducing agents. The reaction mixture is stirred, heated, filtered, concentrated by evaporation, dried by evaporation at ambient or reduced pressure, and further dried at elevated temperature. The precipitate optionally may be washed with water prior to drying.

The complete reaction time may vary from about 15 mins to about 24 hours. In certain embodiments, the drying at elevated temperature time is approximately 30 minutes to 12 hours. The drying temperature can be about 35° C. to about 100° C. and in certain embodiments is about 60° C. to about 90° C. It is important that the drying temperature be elevated to assist in drying the zirconium polymer compositions but not so high that it calcines the composition.

The zirconium polymer composition as made and described herein then can be used for treating gaseous or aqueous mixtures to remove biological contaminants, including bacteria and/or virus.

In certain embodiments, the metal particles can be silver (Ag) and the diffraction peaks for metallic silver can be seen by x-ray diffraction (XRD). In these embodiments, $AgNO_3$ may be used as the soluble metal salt in the methods of making the composition. In certain of these embodiments, the polymeric zirconium can be polymeric zirconium nitrate and a zirconyl nitrate solution may be used in the methods of making the composition.

In the above embodiments with silver metal particles, the silver content of the overall composition is 0.001% by weight to about 30% by weight of the composition. In certain embodiments, the silver is about 0.05% to about 15% by weight of the composition. In other embodiments, the silver is about 0.05% to about 10% by weight of the composition. In further embodiments, the silver is about 0.05% to about 5% by weight of the composition.

In alternative embodiments of the methods for making the zirconium polymer compositions, the metal particles supported on the polymeric zirconium can be formed prior to or during the formation of the zirconium polymer composition. In these embodiments, the metal particles are formed by reductive methods known to those skilled in the art and then combined with the polymeric zirconium. Methods for metal particle formation include hydrothermal reduction.

As described herein, the zirconium polymer compositions have antimicrobial activity, including antibacterial, antiviral, and/or antifungal activity. As such, the zirconium polymer compositions are capable of removing biological contaminants from fluids, including liquids and air. Specifically, the zirconium polymer composition is capable of removing bacteria, viruses, and other microbial contaminants from air and aqueous liquid streams.

Treatment Methods Using the Zirconium Polymer Composition

The present application relates to methods of treating biological contaminated air or liquids (e.g., water) with the zirconium polymer composition containing a polymeric zirconium oxychloride, polymeric zirconium acetate, or polymeric zirconium nitrate and having metal particles thereon. In some embodiments the metal particles are silver. Using this zirconium polymer composition to treat biological contaminated air or water allows for the efficient operation of the air or water treatment method and provides a treated stream with reduced concentrations of biological contaminant. This treated stream can have a biological contaminant that is reduced to or below a target level or can be reduced to a level below which it is detectable.

In certain embodiments, these methods remove biological contaminants from a gaseous stream. The method comprises providing the zirconium polymer composition as described herein; contacting the zirconium polymer composition with a biological contaminant-containing gaseous stream, wherein the biological contaminant is selected from the group consisting of a bacterium, a yeast, an algae, a virus, and mixtures thereof; and removing at least about 75%, or at least about 80%, or at least about 85%, or at least about 90%, or at least about 95%, or at least about 99% of the biological contaminant. In the most efficient embodiments, the biological contaminant is removed at least about 95%.

In other embodiments, these methods remove biological contaminants from an aqueous stream. The method comprises providing the zirconium polymer composition as described herein; contacting the zirconium polymer composition with a biological contaminant-containing gaseous stream, wherein the biological contaminant is selected from the group consisting of a bacterium, a yeast, an algae, a virus, and mixtures thereof; and removing at least about 75%, or at least about 80%, or at least about 85%, or at least about 90%, or at least about 95%, or at least about 99% of the biological contaminant. In the most efficient embodiments, the biological contaminant is removed at least about 95%.

In some embodiments, a biological contaminant-containing gaseous stream is passed through an inlet into a vessel at a temperature and pressure, usually at ambient temperature and pressure, such that the gas in the biological contaminant-containing gaseous stream remains in the gaseous state. In this vessel the biological contaminant-containing gaseous stream is contacted with the zirconium polymer composition comprising a polymeric zirconium oxychloride, polymeric zirconium acetate, or polymeric zirconium nitrate and having metal particles thereon. The contacting of the zirconium polymer composition with the biological contaminant-containing gaseous stream leads to the biological contaminant one or more of sorbing and/or reacting with the metal particles. The sorbing and/or reacting of the biological contaminant with the metal particles of the zirconium polymer composition removes the biological contaminant from the biological contaminant-containing gaseous stream. The biological contaminant may be removed to a target level or to below a target level. In some embodiments the biological contaminant may be removed to a level at which it is undetectable.

In some embodiments, a biological contaminant-containing aqueous stream is passed through an inlet into a vessel at a temperature and pressure, usually at ambient temperature and pressure, such that the water in the biological contaminant-containing aqueous stream remains in the liquid state. In this vessel the biological contaminant-containing aqueous stream is contacted with the zirconium polymer composition comprising a polymeric zirconium oxychloride, polymeric zirconium acetate, or polymeric zirconium nitrate and having metal particles thereon. While not wanting to be bound by any theory, it is believed that the contacting of the zirconium polymer composition with the biological contaminant-containing aqueous stream leads to the biological contaminant one or more of sorbing and/or reacting with the metal particles. The sorbing and/or reacting of the biological contaminant with the metal particles of the zirconium polymer composition removes the biological contaminant from the biological contaminant-containing aqueous stream. The biological contaminant may be removed to a target level or to below a target level. In some embodiments the biological contaminant may be removed to a level at which it is undetectable.

In some embodiments, the zirconium polymer composition metal nanoparticles supported on polymeric zirconium composition comprising a polymeric zirconium oxychloride, polymeric zirconium acetate, or polymeric zirconium nitrate and having metal particles is slurried with a biological contaminant-containing aqueous stream. It can be appreciated that the metal particles of the zirconium polymer composition and the biological contaminant-containing aqueous stream are contacted when slurried. Following the slurring and/or contacting of the zirconium polymer composition having metal particles thereon with the biological contaminant-containing stream, the slurry is filtered by any known solid liquid separation method. While not wanting to be bound by any theory, it is believed that the contacting of the metal particles of zirconium polymer composition with the biological contaminant, leads to the biological contaminant one or more of sorbing and/or reacting with the metal particles. The sorbing and/or reacting of the biological contaminant with the metal particles of the zirconium polymer composition removes the biological contaminant from the biological contaminant-containing aqueous stream. The biological contaminant may be removed to a target level or to below a target level. In some embodiments the biological contaminant may be removed to a level at which it is undetectable.

In other embodiments, the contact is made by contact of the stream with a support material containing the polymeric zirconium compositions. The support material can be polyethylene and the polymeric zirconium compositions can be deposited on the surface or within the polyethylene. When used with polyethylene, the polymeric zirconium compositions having metal particles thereon can be incorporated into a plastic container or a plastic to be incorporated into a high touch surface, such as elevator buttons, escalator railing covers, stair railing covers, touch pads, and the like.

While not wanting to be bound by any theory, it is believed that some, if not most or all, of the biological contaminant contained in the biological contaminant-containing stream is removed from the biological contaminant-containing stream by contacting of the metal particles of the zirconium polymer composition with the biological contaminant-containing stream.

In some embodiments, the zirconium polymer composition is in the form of a fixed bed. The zirconium polymer composition can have any shape or form that exposes a maximum of the metal particles thereon to the gaseous or aqueous stream with minimal back-pressure and the flow of the gaseous or aqueous stream through the fixed bed. In alternative embodiments, the zirconium polymeric composition may be in the form of a shaped body, such as beads, extrudates, porous polymeric structures, or monoliths. In other embodiments, the zirconium polymer composition can be supported as a layer and/or coating on such beads, extrudates, porous polymeric structures, or monolith supports.

In embodiments using a support material, the zirconium polymer composition can be deposited on the support material. The zirconium polymer composition can be deposited on one or more external and/or internal surfaces of the support material. It can be appreciated that persons of ordinary skill in the art generally refer to the internal surfaces of the support material as pores. The zirconium polymer composition can be supported on the support material with or without a binder. In some embodiments, the zirconium polymer composition can be applied to the support material using any conventional techniques, such as slurry deposition.

The contacting of the zirconium polymer composition with the biological contaminant-containing stream normally takes place at a temperature from about 1 to about 100 degrees Celsius, more normally from about 5 to about 40 degrees Celsius. In certain embodiments, the contacting occurs at approximately room temperature (about 18 to about 25 degrees Celsius). Furthermore, the contacting of zirconium polymer composition with the biological contaminant-containing stream commonly takes place at a pH of about 1 to about 11, and more commonly at a pH of about 3 to about 9. The contacting of the zirconium polymer composition with biological contaminant-containing stream generally occurs over a period of time of about 30 seconds to about 24 hours, and more generally for a period of time of about 30 seconds to about 5 hours.

The method of treating air or water to remove biological contaminants comprises the steps of contacting the zirconium polymer composition with the air or water stream containing an initial concentration of undesired biological contaminants and obtaining a treated (or contacted) air or water stream having a concentration of one or more undesired biological contaminants less than the initial concentration.

The contaminants to be removed include bacteria, viruses, fungi, and the like. These bacteria include gram positive and gram negative bacteria and include for example, *Streptococcus, Staphylococcus, E. coli, Escherichia coli*, Methicillin-resistant *Staphylococcus aureus* (MRSA), and the like. These viruses include for example coronaviruses, vaccinia, poliovirus, morbillivirus, and the like. Other microbial contaminants include for example *Trichophyton mentagrophytes*.

In certain embodiments, the biological contaminants to be removed from the air or water stream are viruses. Treating an air or water stream by contacting it with the zirconium polymer composition provides an air or water stream with a reduced concentration of viruses to be removed in comparison to the initial air or water feed. The contacted (or treated) stream can have a concentration of virus equal to or less than a target concentration of virus.

In certain embodiments, the biological contaminants to be removed from the air or water stream are bacteria. Treating an air or water stream by contacting it with the zirconium polymer composition provides an air or water stream with a reduced concentration of bacteria to be removed in comparison to the initial air or water feed. The contacted (or treated) stream can have a concentration of bacteria equal to or less than a target concentration of bacteria.

In certain embodiments, the biological contaminants to be removed from the air or water stream are amoeba. Treating an air or water stream by contacting it with the zirconium polymer composition provides an air or water stream with a reduced concentration of amoeba to be removed in comparison to the initial air or water feed. The contacted (or treated) stream can have a concentration of amoeba equal to or less than a target concentration of amoeba.

The concentration of contaminant in the contacted or treated gaseous or liquid stream can be about 45 colony forming units (CFU)/ml to $5 \times 10^5$ CFU/ml. The target concentration can be set at a certain amount of contaminant (e.g., virus, bacteria, amoeba) CFU per ml or can be set at the limit of detection.

The target concentration also can be set as a percentage reduction of the contaminant in the treated stream versus the concentration in the original stream/feed. In certain embodiments, the concentration of contaminant in the treated stream can be 0.5% to about 100% less than the feed concentrate. In certain embodiments, the treated stream concentration of contaminant is about 5 to about 100% less than the feed concentration, and typically is about 50 to about 100% less than the feed concentration. In certain embodiments, the treated stream concentration of contaminant is about 75 to about 100% less than the feed concentration.

In the methods as described herein, typically the contacting of the zirconium polymer compositions containing polymeric zirconium oxychloride, polymeric zirconium acetate, or polymeric zirconium nitrate and having metal particles thereon with the gaseous or liquid stream reduces the biological contaminant level in the gaseous or liquid stream by more than about 75%. More typically, the contacting of the polymeric zirconium composition with the gaseous or aqueous stream can reduce the biological contaminant level in the gaseous or liquid stream by more than about 80%, more typically more than about 85%, more typically more than about 90%, more typically more than about 95%, more typically more than about 97.5%, more typically more than about 99%, and even more typically more than about 99.5%.

EXAMPLES

The following Examples are provided to illustrate the inventive metal supported on polymeric zirconium composition and methods in more detail, although the scope of the invention is never limited thereby in any way.

Example 1

A silver supported on polymeric zirconium composition was prepared by the following method. 3.8 g of polyurethane diol was dissolved in 60 ml DI water at 50° C. and stirred. To the polyurethane diol solution, 2.2 g $AgNO_3$ crystals, 7.8 g ascorbic acid, 26.4 g zirconyl nitrate solution (ZON) (246 g/l $ZrO_2$ oxide basis) and 0.4 g citric acid were added. The color of the solution went from clear to metallic silver/grey with stirring. After agitating for about 30 mins and then dried on a rotary evaporator under reduced pressure, the product turned to yellow in color. After this dehydration technique, not limited to vacuum or spray drying methods at bulk scale manufacture, the material was successively dried in a tray oven overnight at 90° C. at which point the material is a reddish-brown color.

Analysis of the material by ICP-MS determined the material was 8.2% Ag and 17.35% $ZrO_2$.

Figure 2:
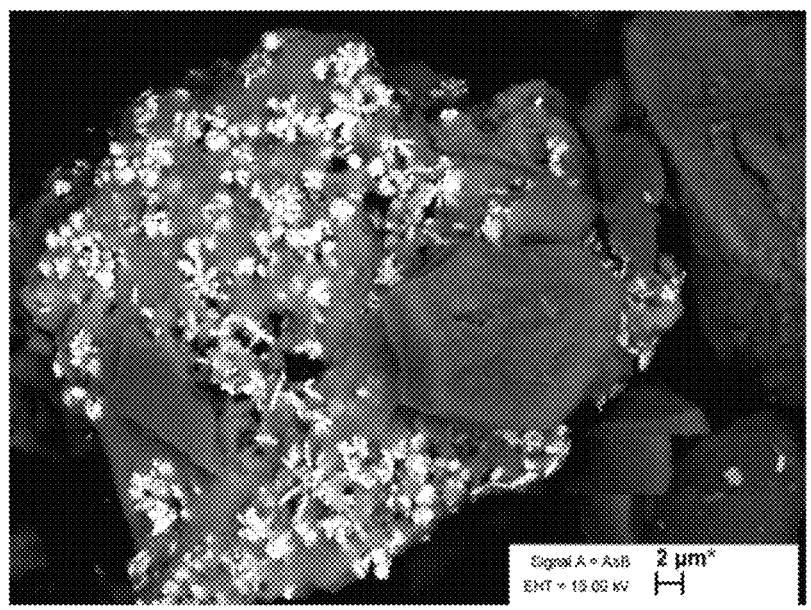
FIG. 2 is a SEM image of the composition of Example 1 with a scale bar of 2 μm.
Figure 3:
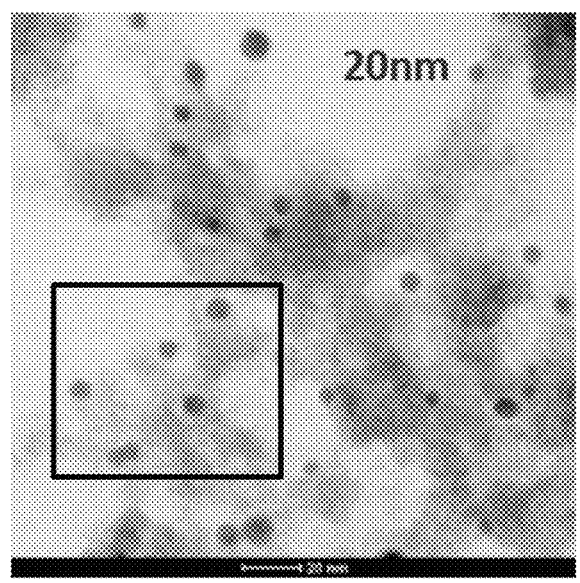
Figure 4:
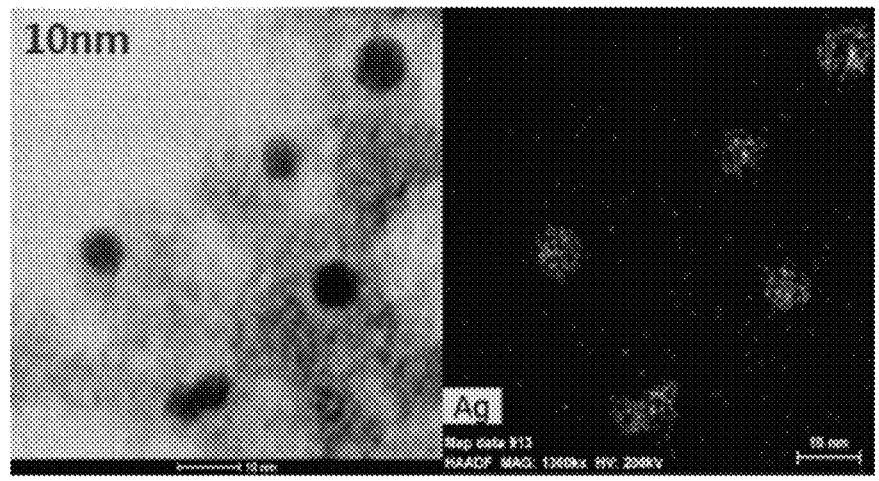
Figure 5:
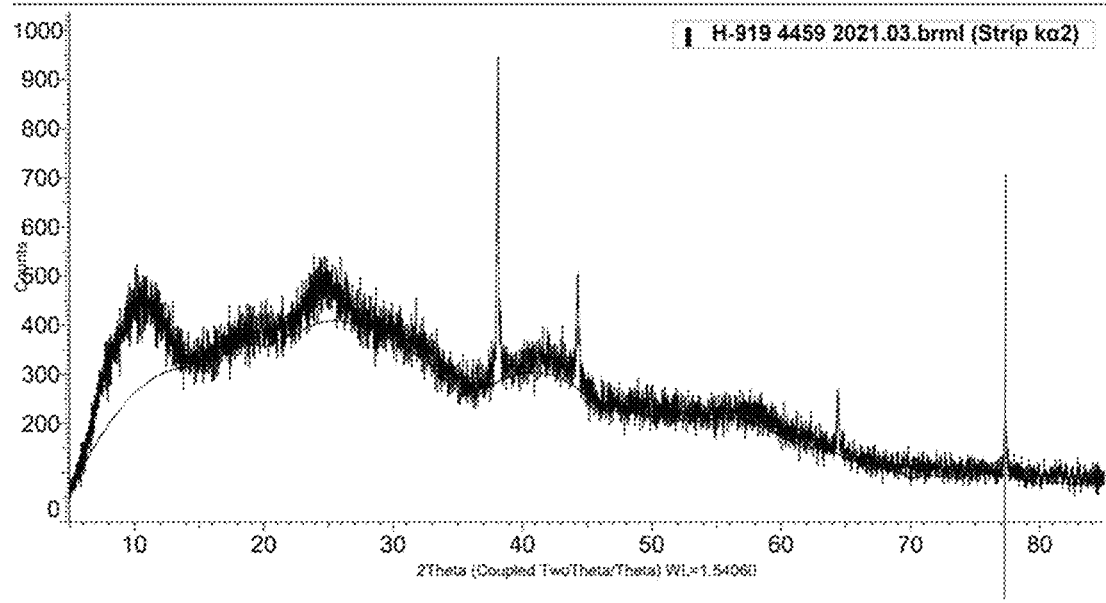
Figure 6:
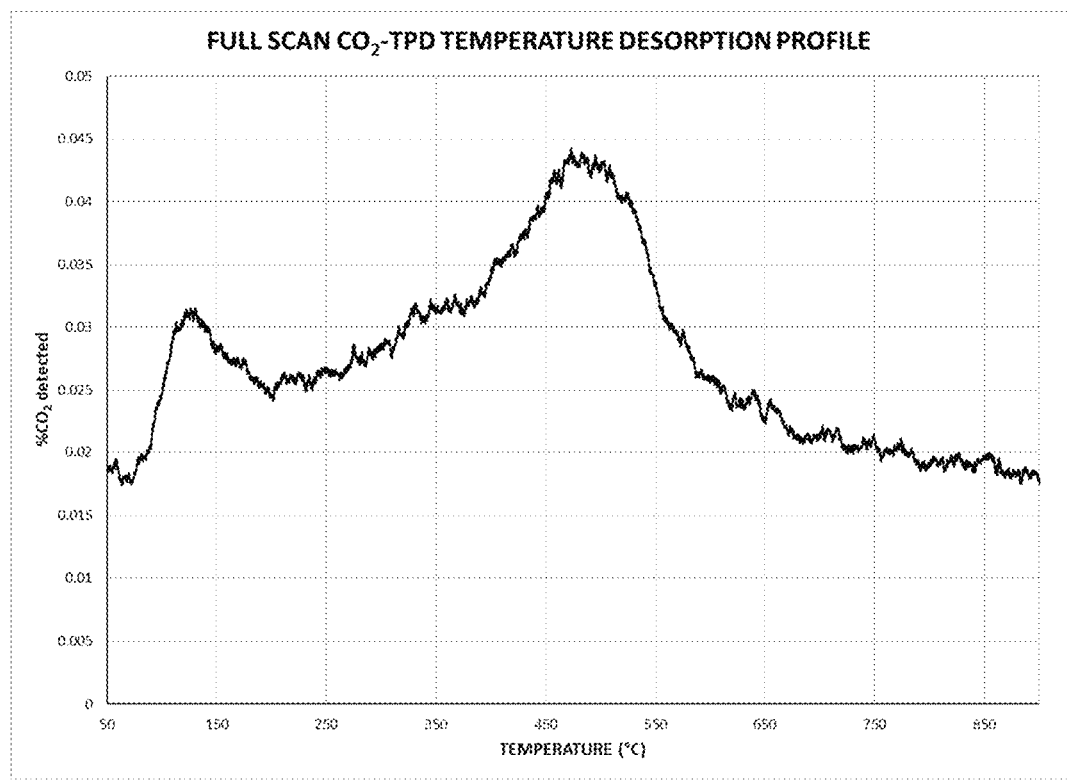
Figure 7:
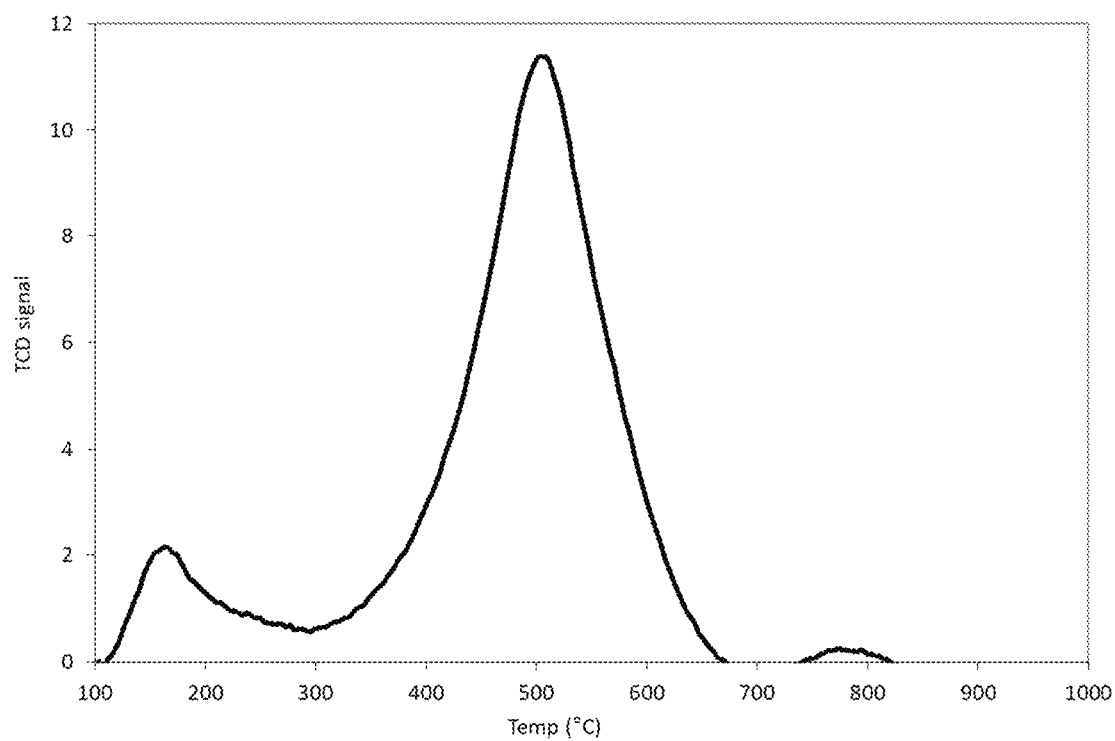

Scanning electron microscope (SEM) images for a sample of the silver nanoparticle supported on polymeric zirconium composition were collected. FIGS. 1 and 2 are the images. The images reveals a very porous structure with what appears to be crystals on the surface. Transmission electron microscope (TEM) images for a sample of the silver nanoparticle supported on polymeric zirconium composition were collected. FIGS. 3 and 4 are the images. FIG. 3 also includes the mapping for Ag. The images reveal a porous structure with Ag dispersed over the surface. A sample of the silver nanoparticle supported on polymeric zirconium composition was analyzed by XRD. FIG. 5 is the XRD pattern. The peaks in the XRD pattern corresponding to Ag metal with peaks at 38, 44, 64, and 77 2Theta. The peak at 38 was quite intense which indicates the 111 lattice plane is oriented parallel to the surface of the support. A sample of the silver nanoparticle supported on polymeric zirconium composition was analyzed for surface area, pore radius, and pore volume by the BET/BJH method (ASTM D3663-20). The surface area was found to be 26.463 $m^2/g$ (BET) and 35.857 $m^2/g$ (BJH). The pore radius was found to be 1.969 Å. And the pore volume was found to be 0.075 cc/g. The temperature programmed desorption of $CO_2$ was performed as described in Hakim, A. et al. Temperature Programmed Desorption of Carbon Dioxide for Activated Carbon supported Nickel Oxide: The Adsorption and Desorption Studies, Advanced Materials Research, Vol. 1087 (2015) pp 45-49. The temperature programmed desorption profile is FIG. 6. The desorption of $CO_2$ had 2 peak temperatures 126° C. and 482° indication both physisorption and chemisorption of $CO_2$. The hydrogen temperature programmed reduction was performed as described in Hurst, N. W. et al. Temperature Programmed Reduction. Catalysis Reviews Science and Engineering, 24:2, 233-309. The hydrogen temperature programmed reduction profile is FIG. 7. Two peaks were observed occurring at approximately 175° C. and 500° C.

Example 2

A silver supported on polymeric zirconium composition was prepared by the following method. 3.8 g of polyvinyl alcohol was dissolved in 60 ml DI water at 50° C. and stirred. To the polyvinyl alcohol comprising solution, 2.2 g $AgNO_3$ crystals, 7.8 g ascorbic acid, 26.4 g zirconyl nitrate solution (ZON) (246 g/l $ZrO_2$ oxide basis) and 0.4 g citric acid were added. The color of the solution went from clear to metallic silver/grey with stirring. After agitating for about 30 mins and then dried on a rotary evaporator under reduced pressure, the product turned to brown in color. After this dehydration technique, not limited to vacuum or spray drying methods at bulk scale manufacture, the material was successively dried in a tray oven overnight at 90° C. Analysis of the material by ICP-MS determined the material was 6.9% Ag and 17.6% $ZrO_2$.

Example 3

A silver supported on polymeric zirconium composition was prepared by the following method. 1.9 g of polyvinylpyrrolidone (~10 k molecular weight) was dissolved in 30 ml DI water at 50° C. and stirred. To the polyvinylpyrrolidone solution, 1.1 g $AgNO_3$ crystals, 3.9 g ascorbic acid, 16.4 g zirconyl nitrate solution (ZON) (246 g/l $ZrO_2$ oxide basis) and 0.2 g citric acid were added. The color of the solution went from clear to metallic silver/grey with stirring. After agitating for about 30 mins and then dried on a rotary evaporator under reduced pressure, the product turned to dark brown in color. After this dehydration technique, not limited to vacuum or spray drying methods at bulk scale manufacture, the material was successively dried in a tray oven overnight at 90° C. Analysis of the material by ICP-MS determined the material was 5.6% Ag and 22% $ZrO_2$.

Example 4

A silver supported on polymeric zirconium composition was prepared by the following method. 1.9 g of polyvinylpyrrolidone (~360 k molecular weight) was dissolved in 30 ml DI water at 50° C. and stirred. To the polyvinylpyrrolidone solution, 1.1 g $AgNO_3$ crystals, 3.9 g ascorbic acid, 16.4 g zirconyl nitrate solution (ZON) (246 g/l $ZrO_2$ oxide basis) and 0.2 g citric acid were added. The color of the solution went from clear to metallic silver/grey with stirring. After agitating for about 30 mins and then dried on a rotary evaporator under reduced pressure, the product turned to yellow in color. After this dehydration technique, not limited to vacuum or spray drying methods at bulk scale manufacture, the material was successively dried in a tray oven overnight at 90° C. Analysis of the material by ICP-MS determined the material was 5.7% Ag and 22% $ZrO_2$.

Example 5

A silver supported on polymeric zirconium composition was prepared by the following method. 1.9 g of polyurethane diol was dissolved in 30 ml DI water at 50° C. and stirred. To the polyurethane diol solution, 1.1 g $AgNO_3$ crystals, 3.9 g ascorbic acid, 13.2 g zirconyl nitrate solution (ZON) (246 g/l $ZrO_2$ oxide basis) and 0.2 g citric acid were added. The color of the solution went from clear to metallic silver/grey with stirring. After agitating for about 30 mins and then dried on a rotary evaporator under reduced pressure, the product turned to yellow in color. After this dehydration technique, not limited to vacuum or spray drying methods at bulk scale manufacture, the material was successively dried in a tray oven overnight at 60° C. and the color remained yellow.

Analysis of the material by ICP-MS determined the material was 9.2% Ag and 14.7% $ZrO_2$.

Example 6

A silver supported on polymeric zirconium composition was prepared by the following method. 3.8 g of polyurethane diol was dissolved in 60 ml DI water at 50° C. and stirred. To the polyurethane diol comprising solution, 2.2 g $AgNO_3$ crystals, 7.8 g ascorbic acid, 26.4 g zirconyl nitrate solution (ZON) (246 g/l $ZrO_2$ oxide basis) and 0.4 g citric acid were added. The color of the solution went from clear to metallic silver/grey with stirring. After agitating for about 30 mins and then dried on a rotary evaporator under reduced pressure, the product turned to brown in color. After this dehydration technique, not limited to vacuum or spray drying methods at bulk scale manufacture, the material was successively dried in a tray oven overnight at 90° C. The material was then washed with water and re-dried at 90° C.

Analysis of the material by ICP-MS determined the material was 7.7% Ag and 49.2% $ZrO_2$.

Example 7

Bacterial Removal Characteristics of the Silver Supported on Polymeric Zirconium Compositions. On the day of the study, the bacteria culture was examined for purity and concentration. The referenced bacteria (Methicillin-resistant *Staphylococcus aureus* or *Escherichia coli*) was homogenized for 30 seconds and allowed a 15-minute rest. The microbial challenge was checked for purity, and then diluted in phosphate buffered saline (PBS). The test was then performed in duplicate as follows: One hundred microliters of a single diluted bacterial species suspension was added to a 50 mL conical tubes (Corning) containing 0.25 g of the selected silver zirconium composition suspended in 25 mL of Sterile DI Water and a NIST traceable laboratory timer was started immediately. The mixture was homogenized at medium speed by vortexing periodically for the desired total contact time. Immediately following, 1 mL of the sample was transferred to a fresh 50 mL tube containing 9 mL of D/E Neutralizing Broth (Criterion) and homogenized. The samples analyzed on the day of the study directly and at various dilutions in replicates of at least 2. Positive and negative controls were performed along with the test subjects to provide quality control and reference data as per laboratory standard accredited IS017025:2017 methodology. Bacteria were analyzed and enumerated as Colony Forming Units (CFU) on the respective media as per SM 9215C. The respective percent reductions were determined based on the recovery of the positive controls and test samples.

TABLE 1

Reduction of MRSA by the silver supported on polymeric zirconium compositions.

| Material of Example | Contact time | Initial MRSA CFU concentration before treatment with the composition (CFU/mL) | Final MRSA CFU concentration after treatment with the composition (CFU/mL) | % reduction |
|---|---|---|---|---|
| 1 | 30 seconds | $1.10 \times 10^4$ | $5.1 \times 10^3$ | 46.7%/log0.27 |
| 1 | 5 min | 11363 | 10147 | 89.3%/log0.97 |
| 1 | 30 mins | $1.10 \times 10^4$ | <0.45 | >99.996%/log4.4 |
| 2 | 30 seconds | $4.91 \times 10^5$ | 1840 | 99.6%/log2.4 |
| 2 | 5 min | $5.00 \times 10^5$ | 192 | 99.96%/log3.4 |
| 2 | 30 mins | $1.55 \times 10^5$ | <0.45 | >99.9997%/>log5.5 |
| 4 | 5 | $1.0 \times 10^5$ | $4.1 \times 10^3$ | 96%/log1.4 |
| 5 | 5 | $1.1 \times 10^4$ | $2.0 \times 10^3$ | 82.6%/log0.76 |
| 6 | 5 | $1.0 \times 10^5$ | $3.1 \times 10^3$ | 96.9%/log3.4 |

TABLE 2

Reduction of *E. coli* by the silver zirconium supported on polymeric compositions.

| Material of Example | Contact time | Initial *E. coli* CFU concentration before treatment with the composition (CFU/mL) | Final *E. Coli* CFU concentration after treatment with the composition (CFU/mL) | % reduction |
|---|---|---|---|---|
| 1 | 30 seconds | $6.55 \times 10^3$ | $3.4 \times 10^3$ | 48.6%/log0.29 |
| 1 | 5 min | $6.55 \times 10^3$ | <0.45 | >99.993%/log4.2 |
| 2 | 30 seconds | $5 \times 10^3$ | 52.7 | 98.9%/log2.0 |
| 2 | 5 min | $2 \times 10^3$ | <0.45 | >99.97%/log3.5 |

TABLE 2-continued

Reduction of E. coli by the silver zirconium supported on polymeric compositions.

| Material of Example | Contact time | Initial E. coli CFU concentration before treatment with the composition (CFU/mL) | Final E. Coli CFU concentration after treatment with the composition (CFU/mL) | % reduction |
|---|---|---|---|---|
| 4 | 5 | $1.5 \times 10^5$ | $1.2 \times 10^4$ | 92.1%/log1.1 |
| 6 | 5 | $1.5 \times 10^5$ | $4.4 \times 10^3$ | 97%/log1.5 |

Example 8

Viral Removal Characteristics of the Silver Supported on Polymeric Zirconium Compositions. A quantitative suspension test for the evaluation of virucidal activity in the medical area was performed. An enveloped DNA virus—vaccinia, a coronavirus surrogate, was selected for screening and comprised a cell culture medium of: Eagle's Minimum Essential Medium (EMEM)+10% FBS+2% Pen/Strep (Culture Media), EMEM+2% FBS+2% FCS+1% Pen/Strep (Viral Media). The product test concentration was 0.1±0.01 g/mL-1 and distilled water was used as the diluent. The suspended powder was liquid vortexed to uniformity. Contact analysis across two soak times of 30±5 minutes & 4±0.3 hours was conducted. The test temperature was maintained at 20±2° C. with an incubation condition of 37±2° C. and 5% $CO_2$. There were no interfering substances and the test products appeared normal and stable. The activity suppression method was one of dilution in ice-cold medium to promote passive settling. No filtration was used.

TABLE 3

Reduction of Vaccinia by the silver supported on polymeric zirconium composition.

| Material of Example | Contact time | Interference Control | Suppression Control | % reduction |
|---|---|---|---|---|
| 2 | 30 mins | Pass | Fail | >99.9%/>log3 |
| 2 | 4 hours | Pass | Fail | >99.9%/>log3 |

An interference and suppression control were tested. The silver supported on polymeric zirconium composition had no interfering effects on the cell monolayer, and whilst it failed its suppression control (had residual activity after being diluted), an alteration to the protocol, such as a higher initial dilution, will be required to mitigate any residual activity.

Example 9

Viral Removal Characteristics of the Silver Supported on Polymeric Zirconium Compositions. An aliquot of the referenced virus was added to Sterile DI Water and homogenized. 25 mL of the prepared test water was added to a 50 mL conical tubes (Corning) containing 0.25 g of the test material and a NIST traceable laboratory timer was started immediately. The mixture was homogenized at medium speed on an orbital shaker a total contact time of 30-minutes. Immediately following, 1 mL of the sample was transferred to a fresh 50 mL tube containing 9 mL of D/E Neutralizing Broth (Criterion) and homogenized. The recovery control consisted of a sterile tube containing 25 mL of test water that was homogenized and treated in the same manner as the test substances. The samples analyzed on the day of the study directly and at various dilutions in replicates of at least 5. Positive and negative controls were performed along with the test subjects to provide quality control and reference data as per laboratory standard accredited ISO17025:2017 methodology. Poliovirus analysis was conducted using Buffalo Green Monkey (BGM) kidney Cell Monolayers as per method EPA 1615. Briefly, aliquots of a sample containing the virus were inoculated on freshly prepared monolayers of BGM cells. Each sample volume was inoculated in replicates of five. Each sample was analyzed using a minimum of five ten-fold dilutions The cells were then incubated in Dulbecco's Modified Eagle's medium (dMEM, Mediatech Inc, USA) media 2% Fetal Bovine Serum (FBS, Mediatech, USA) at 36.5° C. and 5% $CO_2$ for 5 days. Cells were microscopically monitored routinely for signs of degeneration. Cells in flasks demonstrating signs of infectivity (Cytopathic effects; CPE) were recorded as positive (+) and those that did not demonstrate any CPE were recorded as negative (−). The Most Probable Number (MPN) of virus Infectious Units (IU) in a sample was then calculated using MPN-CALC software (version 0.0.0.23). The respective percent reductions were determined based on the recovery of the positive controls and test samples. Human Coronavirus OC43 (ATCC VR-1558) virus was propagated and enumerated as Most Probable Numbers (MPN) using human ileocecal colorectal adenocarcinoma HCT-8 cell line (ATCC CCL-244) as the host. Cells were grown in 6-well plates cell culture flasks. For enumeration, virus was enumerated as infectious units as per the assay methodology described in Standard Method 9510 (APHA, 2012); the methodology is equivalent to EPA/600/R-95/178 and the updated EPA/600/4-84/013. Briefly, aliquots of a sample containing the virus were inoculated on freshly prepared monolayers of HCT8 cells (approximately 90% confluence). Each sample volume was inoculated in replicates of five. The cells were then incubated in Dulbecco's Modified Eagle's medium (dMEM, Mediatech Inc, USA) media 2% Fetal Bovine Serum (FBS, Mediatech, USA) at 35° C. and 5% $CO_2$ for 8-10 days. Cells were microscopically monitored routinely for signs of degeneration. Cells in flasks demonstrating signs of infectivity (Cytopathic effects; CPE) were recorded as positive (+) and those that did not demonstrate CPE were recorded as negative (−). The most probable number of infectious virus in a sample was then calculated using MPNCALC software (version 0.0.0.23). The respective percent reductions were determined based on the recovery of the positive controls and test samples.

TABLE 4

Reduction of Poliovirus by the silver supported on polymeric zirconium composition.

| Material of Example | Contact time | Initial Poliovirus concentration before treatment with the composition (MPN/mL) | Final Poliovirus concentration after treatment with the composition (MPN/mL) | % reduction |
|---|---|---|---|---|
| 2 | 30 mins | $9.20 \times 10^5$ | 0.2 | 99.99998%/log6.7 |

TABLE 5

Reduction of OC43 by the silver supported on polymeric zirconium composition.

| Material of Example | Contact time | Initial OC43 concentration before treatment with the composition (MPN/mL) | Final OC43 concentration after treatment with the composition (MPN/mL) | % reduction |
|---|---|---|---|---|
| 2 | 30 mins | $1.30 \times 10^5$ | <18 | >99.99%/>log4 |
| 6 | 30 mins | $1.30 \times 10^5$ | 27 | 99.98%/log3.7 |

Example 10

Fungi Removal Characteristics of the Silver Supported on Polymeric Zirconium Compositions. Spores of *Trichophyton mentagrophytes* where prepared as per ASTM E2197 (Standard Quantitative Disk Carrier Test Method for Determining Bactericidal, Virucidal, Fungicidal, Mycobactericidal, and Sporicidal Activities of Chemicals). An aliquot of the spore suspension was added to sterile DI water and homogenized. Each test substance was tested as follows: 25 mL of the prepared test water was added to a 50 mL conical tubes (Corning) containing 0.25 g of a single test substance and a NIST traceable laboratory timer was started immediately. The mixture was homogenized at medium speed on a rotary mixer for a contact time of 5, 30, and 60 minutes. Immediately following each contact time, 1 mL of the sample was transferred to a fresh 50 mL tube containing 9 mL of D/E Neutralizing Broth (Criterion) and homogenized. The recovery control consisted of a sterile tube containing 25 mL of prepared test water that was homogenized and treated in the same manner as the test substances. On the day of the study, the fungal spore suspension was examined for purity and concentration. The samples were analyzed on the day of the study directly and at various dilutions in replicates of at least 2. Positive and negative controls were performed along with the test subjects to provide quality control and reference data as per laboratory standard accredited ISO17025:2017 methodology. Fungi were analyzed and enumerated as Colony Forming Units (CFU) on rose bengal agar (BD Difco) as per SM 9215C. The respective percent reductions were determined based on the recovery of the positive controls and test samples.

TABLE 6

Reduction of Trichophyton mentagrophytes by the silver supported on polymeric zirconium composition.

| Material of Example | Contact time | Initial Trichophyton mentagrophytes concentration before treatment with the composition (CFU/mL) | Final Trichophyton mentagrophytes concentration after treatment with the composition (CFU/mL) | % reduction |
|---|---|---|---|---|
| 2 | 5 mins | $1.10 \times 10^6$ | $1.10 \times 10^4$ | 99.0%/log2 |
| 2 | 30 mins | $1.10 \times 10^6$ | <5 | >99.9995%/>log5.3 |
| 2 | 60 mins | $1.10 \times 10^6$ | <5 | >99.9995%/>log5.3 |
| 3 | 5 mins | $1.10 \times 10^6$ | $2 \times 10^4$ | 98.2%/log1.7 |
| 3 | 30 mins | $1.10 \times 10^6$ | <5 | >99.9995%/>log5.3 |
| 3 | 60 mins | $1.10 \times 10^6$ | <5 | >99.9995%/>log5.3 |
| 4 | 5 mins | $1.10 \times 10^6$ | $7.3 \times 10^3$ | 99.3%/log2.2 |
| 4 | 30 mins | $1.10 \times 10^6$ | <5 | >99.9995%/>log5.3 |
| 4 | 60 mins | $1.10 \times 10^6$ | <5 | >99.9995%/>log5.3 |
| 6 | 5 mins | $1.10 \times 10^6$ | $1.0 \times 10^5$ | 90.9%/log1 |
| 6 | 30 mins | $1.10 \times 10^6$ | $1.0 \times 10^4$ | 99.1%/log2 |
| 6 | 60 mins | $1.10 \times 10^6$ | $6.8 \times 10^2$ | 99.94%/log3.2 |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained.

Notwithstanding that the numerical ranges and parameters setting forth the broad scope of the technology are approximations, the numerical values set forth in the specific examples are reported as precisely as possible. Any numerical value, however, inherently contain certain errors necessarily resulting from the standard deviation found in their respective testing measurements.

It will be clear that the compositions and methods described herein are well adapted to attain the ends and advantages mentioned as well as those inherent therein. Those skilled in the art will recognize that the methods and systems within this specification may be implemented in many manners and as such are not to be limited by the foregoing exemplified embodiments and examples. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope contemplated by the present disclosure. Numerous other changes may be made which will readily suggest themselves to those skilled in the art and which are encompassed in the spirit of the disclosure.

What is claimed is:

1. A solid zirconium polymer composition comprising a dried zirconium polymer selected from the group consisting of polymeric zirconium oxychloride, polymeric zirconium acetate, and polymeric zirconium nitrate, and polyvinylpyrrolidone (PVP), and having metal particles on the surface of the zirconium polymer, wherein the metal is selected from the group consisting of aluminum (Al), antimony (Sb), arsenic (As), barium (Ba), silicon (Si), boron (B), copper (Cu), gold (Au), lead (Pb), mercury (Hg), nickel (Ni), silver (Ag), thorium (Th), tin (Sn), zinc (Zn), and mixtures thereof, and the metal particles are about 0.001% by weight to about 30% by weight of the composition, wherein the composition has biological contaminant removal properties.

2. The composition of claim 1, wherein the metal particles are about 0.05% to about 15% by weight of the composition.

3. The composition of claim 1, wherein the metal particles are about 0.05% to about 10% by weight of the composition.

4. The composition of claim 1, wherein the metal particles are silver.

5. The composition of claim 4, where the silver is metallic.

6. The composition of claim 1, wherein the zirconium polymer is polymeric zirconium nitrate.

7. The composition of claim 6, wherein the polymeric zirconium nitrate has a $NO_3$:Zr molar ratio of about 0.5:1 to about 1.5:1.

8. The composition of claim 1, wherein the metal particles are silver and the zirconium polymer is polymeric zirconium nitrate.

9. The composition of claim 1, further comprising a reducing agent selected from the group consisting of sucrose, ascorbic acid, and mixtures thereof and a chelating agent selected from the group consisting of citric acid, malonic acid, succinic acid, glutaric acid, adipic acid, and mixtures thereof.

10. The composition of claim 1, wherein the composition has a surface area of about 10 $m^2$/g to about 100 $m^2$/g.

11. The composition of claim 1, wherein the composition has a pore volume of about 0.01 $cm^3$/g to about 0.5 $cm^3$/g and an average pore size of about 1 nm to about 25 nm.

12. The composition of claim 1, wherein the composition has a particle size D50 of about 0.5 μm to about 15 μm and a particle size D100 of about 2 μm to about 50 μm.

13. The composition of claim 1, wherein the composition is deposited on or within a support material.

14. A method for making a solid zirconium polymer composition having biological contaminant removal properties comprising:
 (i) dissolving polyvinylpyrroldone (PVP) in water to form a mixture;
 (ii) to the mixture of (i) adding: (a) soluble metal salt wherein the metal is selected from the group consisting of aluminum (Al), antimony (Sb), arsenic (As), barium (Ba), silicon (Si), boron (B), copper (Cu), gold (Au), lead (Pb), mercury (Hg), nickel (Ni), silver (Ag), thorium (Th), tin (Sn), zinc (Zn), and mixtures thereof, (b) a reducing agent, (c) zirconyl nitrate solution, zirconyl chloride solution, or zirconyl acetate solution, and (d) a chelating agent to create a solution;
 (iii) removing liquid of the solution of (ii) to obtain a zirconium polymer precipitate comprising a zirconium polymer selected from the group consisting of polymeric zirconium oxychloride, polymeric zirconium acetate, and polymeric zirconium nitrate, and PVP and having metal particles on the surface of the zirconium polymer; and
 (iv) collecting and drying the zirconium polymer precipitate composition to obtain the solid polymer composition of claim 1.

15. The method of claim 14, wherein the soluble metal salt is $AgNO_3$.

16. The method of claim 14, wherein the reducing agent is selected from the group consisting of sucrose, ascorbic acid, hydrogen gas, hydrazine, and mixtures thereof.

17. The method of claim 14, wherein the drying is at a temperature of about 35° C. to about 100° C.

18. The method of claim 14, wherein the chelating agent is selected from the group consisting of citric acid, malonic acid, succinic acid, glutaric acid, adipic acid, and mixtures thereof.

19. A method for removing biological contaminants from a gaseous stream, comprising:
 providing the zirconium polymer composition of claim 1;
 contacting the zirconium polymer composition with a biological contaminant-containing gaseous stream, wherein the biological contaminant is selected from the group consisting of a bacterium, a yeast, an algae, a virus, and mixtures thereof, and
 removing at least about 99% of the biological contaminant.

20. A method for removing biological contaminants from an aqueous stream, comprising:
 providing the zirconium polymer composition of claim 1;
 contacting the zirconium polymer composition with a biological contaminant-containing aqueous stream, wherein the biological contaminant is selected from the group consisting of a bacterium, a yeast, an algae, a virus, and mixtures thereof; and removing at least about 99% of the biological contaminant.

21. The composition of claim 1, wherein the metal particles are about 5.6% to about 5.7% by weight of the composition.

22. The method of claim 19, wherein the gaseous stream is from building ventilation systems, aircraft ventilation systems, vehicle ventilation systems, or ambient air.

23. The method of claim 20, wherein the aqueous stream is drinking water, well water, lake water, pond water, wetland water, agricultural water, wastewater from industrial processes, or geothermal water.

24. The method of claim 19, wherein the zirconium polymer composition is deposited on or within a support material.

25. The method of claim 20, wherein the zirconium polymer composition is deposited on or within a support material.

26. The method of claim 19, wherein the biological contaminant is removed to a target level or to below a target level.

27. The method of claim 20, wherein the biological contaminant is removed to a target level or to below a target level.

28. The method of claim 19, wherein the biological contaminant is bacteria, viruses, or mixtures thereof.

29. The method of claim 20, wherein the biological contaminant is bacteria, viruses, or mixtures thereof.

\* \* \* \* \*